United States Patent [19]

Maekawa et al.

[11] Patent Number: 4,465,868
[45] Date of Patent: Aug. 14, 1984

[54] PROCESS FOR PREPARING O-METHALLYLOXYPHENOL

[75] Inventors: Tsukasa Maekawa; Takeshi Gondo; Syozo Hayase, all of Tokushima, Japan

[73] Assignee: Otsuka Kagaku Yakuhin Kabushiki Kaisha, Japan

[21] Appl. No.: 387,602

[22] Filed: Jun. 11, 1982

[30] Foreign Application Priority Data

Jul. 17, 1981 [JP] Japan ................................ 56-112823
Jul. 17, 1981 [JP] Japan ................................ 56-112824
Mar. 16, 1982 [JP] Japan ................................ 57-41872

[51] Int. Cl.$^3$ ............................................. C07C 41/16
[52] U.S. Cl. .................................................... 568/652
[58] Field of Search ......................................... 568/652

[56] References Cited

U.S. PATENT DOCUMENTS

| | | | |
|---|---|---|---|
| 3,474,170 | 10/1969 | Scharpf | 424/285 |
| 3,474,171 | 10/1969 | Scharpf | 424/285 |
| 3,927,118 | 12/1975 | Ozretich | 568/652 |
| 4,250,333 | 2/1981 | Rakoutz | 568/652 |
| 4,252,985 | 2/1981 | Rakoutz | 568/652 |
| 4,263,462 | 4/1981 | Michelet et al. | 568/652 |
| 4,314,086 | 2/1982 | Soula et al. | 568/652 |

FOREIGN PATENT DOCUMENTS 2932458 2/1981 Fed. Rep. of Germany .

*Primary Examiner*—Bernard Helfin
*Attorney, Agent, or Firm*—Larson and Taylor

[57] ABSTRACT

A process for preparing o-methallyloxyphenol characterized in that catechol and methallyl chloride are reacted with use of:

A. at least one base selected from among carbonates and bicarbonates of alkali metals, bicarbonates of alkaline earth metals and amines at least 10 in pKa, B. at least one catalyst selected from among iodides of alkali metals or alkaline earth metals, hydrogen iodide and methallyl iodide, and C. a ketone solvent or ketone-water mixture solvent.

17 Claims, 1 Drawing Figure

FIG 1

PROCESS FOR PREPARING O-METHALLYLOXYPHENOL

This invention relates to an improvement in a process for preparing o-methallyloxyphenol from catechol and methallyl chloride.

o-Methallyloxyphenol is a known compound useful as a material for carbofuran insecticidal compositions. It is known that when subjected to a rearrangement and cyclization reaction, the compound gives 2,3-dihydro-2,2-dimethyl-7-hydroxybenzofuran useful as a material for agricultural chemicals. Although various processes have been developed for preparing o-methallyloxyphenol (hereinafter referred to as "monoether") from catechol and methallyl chloride, the conventional processes are low in the yield of the desired monoether or are uneconomical even if high in the yield because the processes form o-dimethallyloxybenzene (hereinafter referred to as "diether") as a by-product, permit oxidation of catechol or afford large amounts of dimer and like polymers thereof.

While phenol or like monohydroxybenzene can be etherified usually easily in good yields without any particular difficulty, extreme difficulty is encountered in etherifying catechol or like dihydroxybenzene when it is attempted to etherify only one of the hydroxyl groups selectively since both hydroxyl groups can participate in the etherification. Further when the etherifying reagent has relatively low reactivity like alkyl derivatives, there is a reduced likelihood or alkylation of the benzene nucleus, whereas if the etherifying agent used is an allyl derivative which is more reactive than alkyl derivatives, notably methallyl chloride, alkylation of the benzene nucleus occurs which is extremely difficult to control. Consequently the formation of the diether and derivatives having an alkylated benzene nucleus reduces the yield of the monoether and produces a mixture of such products. It is difficult and uneconomical to separate the monoether from this mixture. Given below are the conventional techniques for producing the monoether from catechol and methallyl chloride.

(1) Published Examined Japanese Patent Application No. 12263/1967 (U.S. Pat. No. 3,474,171)

These publications disclose the most rudimentary technique wherein equimolar amounts of catechol and methallyl chloride are reacted in dry acetone in the presence of $K_2CO_3$ and KI under reflux for 30 hours to obtain the monoether. However, no discussion is presented on the amounts of acetone, base and catalyst to be used. The yield attained is as low as 45%, while the publications suggest nothing about how to inhibit the formation of the diether to obtain the desired monoether in a high yield.

(2) Published Unexamined Japanese Patent Application No. 95230/1975 and (U.S. Pat. No. 3,927,118)

These publications disclose a process for selectively monoetherifying dihydroxybenzenes characterized in that a hydroxyphenol is reacted with an alkylating agent in the presence of an alkaline earth metal hydroxide or oxide in a dipolar aprotic solvent having a sulfoxide, sulfone or amide group. Thus the process uses the specified solvent which is relatively expensive and has a high boiling point. It is understood from examples given in the specifications that up to 0.5 mole of methallyl chloride is used per mole of catechol to selectively monoetherify the starting material. However, the monoether yield of this process is invariably less than 50% and is actually as low as less than 40%. The process has another drawback in that the recovery of unreacted expensive catechol from the reaction mixture requires an exquisite and expensive separating treatment.

(3) Published Unexamined Japanese Patent Application No. 106438/1979 (U.S. Pat. No. 4,250,333)

The process disclosed is intended to avoid the drawback resulting from the use of a large excess of catechol and is characterized by using aprotic solvent containing an amido, sulfoxide, ether or like group, especially N-methyl-pyrrolidone, and a specified quantity of an alkali metal carbonate or bicarbonate. This process produces the diether in a relatively large quantity and involves difficulty in separating the monoether from the selected solvent by distillation because the monoether is thermally instable and because the solvent is high boiling.

(4) Published Unexamined Japanese Patent Application No. 7291/1980 (U.S. Pat. No. 4,252,985)

The process disclosed is characterized by reacting catechol with methallyl chloride in a two-phase reaction medium comprising water and a water-immiscible inactive organic solvent having a boiling point of at least 50° C., in the presence of a quaternary ammonium derivative or phosphonium derivative. The process is generally low in the yield of the monoether based on the starting material, i.e. catechol, and requires the use of the above-mentioned special compound, i.e. quaternary ammonium derivative or phosphonium derivative, as a phase-transfer catalyst.

(5) Published Unexamined Japanese Patent Application No. 76833/1980 (U.S. Pat. No. 4,263,462)

The publications disclose a considerably complex process comprising the steps of mixing together the starting materials, a base, and a quaternary ammonium derivative or phosphonium derivative in a first zone having two phases, i.e. an organic solvent and water, separating the organic phase from the aqueous phase, and heating the organic phase at a reaction temperature in a second zone to obtain the monoether. This process is basically the same as the one disclosed in the foregoing Japanese Publication 7291/1980, uses the quaternary ammonium derivative or phosphonium derivative and requires a cumbersome procedure wherein the reaction is conducted separately in the first and second zones. Although the examples given reveal high yields of about 90% relative to the converted catechol, the conversions of catechol are as low as about 60% or lower.

(6) Published Unexamined Japanese Patent Application No. 29584/1981 (Laid-Open German Patent Publication No. 2,932,458)

These publications disclose a process for preparing the monoether which uses polyhydroxyalkyl ether having at least one hydroxyl group and serving as a solvent, sodium carbonate, sodium hydrogencarbonate or like base, and sodium dithionite serving as a reducing agent and in which carbon dioxide gas and water are removed from the reaction system. The special solvent, i.e. polyhydroxyalkyl ether, is used, without being recovered, for the subsequent rearrangement and cyclization reaction for preparing 2,3-dihydro-2,2-dimethyl-7-benzofuranol. With this process, the unreacted catechol is transferred to the subsequent reaction, maintained at a high temperature of about 180° C. and therefore difficult to recover for reuse.

The conventional processes for preparing the monoether described above thus use high-boiling solvents which are relatively expensive, or specified quaternary ammonium derivatives or phosphonium derivatives in a two-phase nonhomogeneous reaction system and have the drawbacks mentioned.

An object of the present invention is to provide a process for selectively preparing the desired monoether with use of an inexpensive and readily available solvent by a simple procedure without necessitating any special compound such as quaternary ammonium derivatives or phosphonium derivatives.

Another object of the invention is to provide a process for preparing the desired monoether in which the unreacted materials and catalyst can be recovered for reuse with ease, the process further permitting aftertreatment of the resulting reaction mixture with extreme ease.

The invention provides a process for preparing o-methallyloxyphenol characterized in that catechol and methallyl chloride are reacted with use of:

A. at least one base selected from among carbonates and bicarbonates of alkali metals, bicarbonates of alkaline earth metals and amines at least 10 in pKa,
B. at least one catalyst selected from among iodides of alkali metals or alkaline earth metals, hydrogen iodide and methallyl iodide, and
C. a ketone solvent or ketone-water mixture solvent.

The solvent to be used in this invention is a ketone or, alternatively, a ketone-water mixture.

The reaction to be conducted with use of a ketone solvent will be described first. In this case, the reactivity is greatly influenced by variations in the amounts of the ketone solvent, base and catalyst. In face, we have found that surprising results can be achieved with use of appropriate amounts of these materials, as will be described below more specifically.

Figure 1:
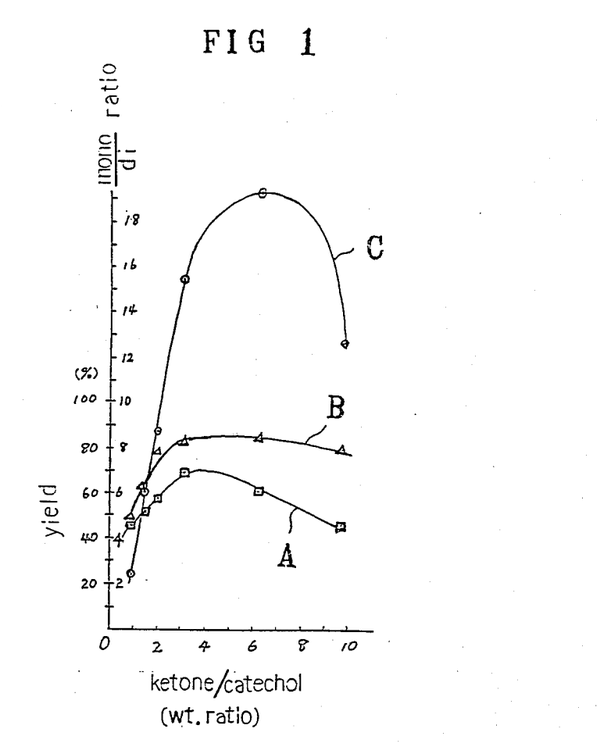

Tables 1 to 3 given below show the results achieved in some of the examples and comparison examples to follow, to reveal the relation of the yield and selectivity of the monoether and the monoether to diether mole ratio (mono/di ratio) achieved, to the amount of a ketone solvent, base or catalyst used. Acetone was used as the ketone solvent, $K_2CO_3$ as the base and KI as the catalyst. Table 1 shows the relation between acetone and the yield. In Comparison Example 1, 0.94 g of acetone was used per gram of catechol. In Examples listed in Table 1, the yield(A), selectivity(B) and mono/di ratio(C) greatly increase with increasing amount of acetone. FIG. 1, which shows this tendency, indicates that the effective amount of acetone is 1 to 10 parts by weight, especially 2 to 7 parts by weight, per part by weight of catechol. The effect becomes more pronounced in any of the yield, selectivity and mon/di ratio with a reduction in the amount of $K_2CO_3$ as well as of KI. With this tendency, the reactivity also improves, such that a satisfactory result can then be achieved within one half the reaction time otherwise needed, hence a double effect.

Tables 2 and 3 show the relation between the yield, etc. and the amount of $K_2CO_3$ or KI. These tables reveal that outstanding results are achievable when 0.3 to 1 mole of $K_2CO_3$ is used per mole of catechol, and also when 0.01 to 1 mole of KI is used per mole of catechol.

The present process to be practiced with use of a ketone-water mixture solvent will now be described. Due to the presence of water in this case, the catalyst and base dissolve in the solvent, so that the etherification can be completed within a short period of time even with use of a small amount of catalyst. With the progress of the reaction, the reaction mixture separates into an ethereal organic solvent and an aqueous layer containing the expensive iodide. When the organic layer is concentrated to remove the ketone and the unreacted methallyl chloride and thereafter distilled in a vacuum, the monoether can be obtained easily with a high quality. On the other hand, the iodide contained in the aqueous layer need not be regenerated and therefore can be recovered almost wholly unlike any other case. The unreacted base remaining in the aqueous layer is of course reusable. According to the invention, it is usually preferable to remove the resulting chloride precipitate from the aqueous layer and then replenish the layer with the base for reuse.

With the above process, the reaction mixture is separated into an aqueous layer and an organic layer. It is desirable to use the aqueous layer as it is again for the reaction, or after treating the layer, for example, in the following manner.

(a) The chloride formed in the aqueous layer is filtered off as solids after cooling, and fresh base is added to the filtrate.

(b) The base is added to the aqueous layer, and the chloride is separated off at the ambient temperature or after cooling as solids.

(c) Sodium carbonate, sodium bicarbonate or sodium hydroxide is added to the aqueous layer to subject the chloride to an exchange reaction to obtain sodium chloride and a base useful as a material. Utilizing the solubility difference due to a change in temperature, the sodium chloride is caused to separate off and then filtered off.

According to the invention, it is desirable to use about 0.6 to about 1.4 moles of methallyl chloride per mole of catechol.

The bases useful for this invention include, for example, carbonates and bicarbonates of alkali metals, bicarbonates of alkaline earth metals, and amines at least 10 in pKa. Examples of useful salts are $K_2CO_3$, $Na_2CO_3$, $KHCO_3$, $NaHCO_3$, $Ca(HCO_3)_2$, etc. Examples of useful amines at least 10 in pKa are cyclic amidines represented by the formula wherein $R^1$ and $R^2$ are each hydrogen or alkyl having 1 to 5 carbon atoms, or are joined together to form alkylene having 2 to 11 carbon atoms, and $R^3$ is alkylene having 2 to 6 carbon atoms, and amines represented by the formula wherein $R^4$ and $R^5$ are each hydrogen, alkyl having 1 to 8 carbon atoms or cycloalkyl having 5 to 8 carbon atoms, or are joined together to form alkylene having 5 to 8 carbon atoms, and $R^6$ is hydrogen, alkyl having 1 to 8 carbon atoms or phenyl.

Examples of such amidines are 1,8-diaza-bicyclo[5,4,0]-7-undecene (DBU), 1,6-diaza-bicyclo-[4,3,0]-

5-nonene, 1,5-diaza-bicyclo[4,2,0]-5-octene, 1,4,-diaza-bicyclo[3,3,0]-4-octene, 3-methyl-1,4-diaza-bicyclo[3,3,0]-4-octene, etc.

Examples of amines of the above formula are ethylamine, diethylamine, triethylamine, cyclohexylamine, butylamine, hexylamine, dicyclohexylamine, methylamine, dimethylamine, piperidine, etc.

According to the invention, alkali metal carbonates or alkaline earth metal bicarbonates are used in an amount of about 0.3 to about 1 mole, preferably about 0.4 to about 0.7 mole, per mole of catechol, or alkali metal bicarbonates are used in an amount of about 0.6 to about 3 moles, preferably about 0.8 to about 1.4 moles, per mole of catechol. About 0.3 to about 3 moles of amines at least 10 pKa are used per mole of catechol.

With the present invention, at least one of iodides of alkali metals or alkaline earth metals, hydrogen iodide and methallyl iodide is usable as a catalyst. Examples of useful iodides of alkali metals and alkaline earth metals are LiI, NaI, KI, RbI, CsI, BeI$_2$, MgI$_2$, CaI$_2$, BaI$_2$, etc., among which KI and NaI are especially preferable.

In the reaction system, the catalyst reacts as represented by Equation (1) to form highly reactive methallyl iodide, which then reacts as shown by Equation (2) to form the monoether, giving the catalyst in the initial state.

Hydrogen iodide, when used, reacts first with the base in the reaction system as represented by Equation (3), giving KI, which thereafter repeatedly undergoes the reactions of Equations (1) and (2).

Methallyl iodide undergoes the reaction of Equation (2), followed by the reactions of Equations (1) and (2) repeatedly.

Usually about 0.01 to about 1 mole, preferably about 0.3 to about 0.7 mole, of the catalyst is used per mole of catechol.

The ketones useful in this invention are those represented by the formula $$R^7COR^8$$

wherein $R^7$ is alkyl having 1 to 6 carbon atoms, $R^8$ is alkyl having 1 to 6 carbon atoms or phenyl, or $R^7$ and $R^8$ may be joined together to form alkylene having 4 to 8 carbon atoms. Examples of useful ketones are acetone, methyl ethyl ketone, diethyl ketone, methyl isobutyl ketone, dipentyl ketone, cyclohexanone, acetophenone, etc.

When such a ketone solvent is used in this invention, it is preferable to use about 1 to about 10 parts by weight of the ketone per part by weight of catechol. Alternatively when a ketone-water mixture solvent is used, it is desirable to use about 1 to about 10 parts by weight of the ketone and about 0.1 to about 10 parts by weight of water, per part by weight of catechol.

The reaction of the invention is conducted preferably at a temperature of about 50° to about 150° C. When the reaction is conducted at an increased pressure, the pressure is not particularly limited since the pressure varies greatly with the kind of the solvent and the reaction temperature.

The present invention can be practiced batchwise or continuously.

The mode of practicing the present invention will be described in greater detail.

The reaction to be carried out with use of a ketone solvent will be described first. Catechol, methallyl chloride and the desired solvent, base and catalyst are wholly mixed together in the desired order while cool, and the mixture is thereafter heated. Alternatively the mixture, other than methallyl chloride, is heated first, and methallyl chloride is thereafter admixed with the hot mixture.

After the reaction, the reaction mixture is cooled to room temperature. Crystals, if present, are filtered off and then washed with a small amount of solvent. The solvent is combined with the filtrate. The crystals comprise, for example, an alkali metal carbonate, alkali metal bicarbonate, alkali metal chloride and alkali metal iodide and are reusable as such or after treatment. The alkali metal chloride, even if contained in a large amount in the crystals, presents no particular problem to the reuse of the crystals. When desired, a small amount of water is added to the crystals, the mixture is heated to cause the salts other than the alkali metal chloride to dissolve in the water while hot utilizing the solubility difference involved, and the small amount of the aqueous solution is removed for the reuse of the crystals.

On the other hand, the solvent and methallyl chloride are removed from the filtrate in a vacuum, and the remaining catechol is extracted from the residue with water. The aqueous layer is reused after a small amount of water is removed therefrom. While the monoether only can be isolated from the oil layer by distillation, the oil layer is usable as it is for the subsequent rearrangement and cyclization reaction for preparing 2,3-dihydro-2,2-dimethyl-7-hydroxybenzofuran.

When a ketone-water mixture solvent is used, the materials may be mixed together in the same manner as when the ketone solvent is used. With the progress of the reaction, the reaction mixture separates into two layers, namely an aqueous layer and an organic layer containing the monoether. While the aqueous layer contains the unreacted base, catalyst and the chloride formed by the reaction, the layer is reused as it is or after being treated by one of the methods (a) to (c)

already described. The organic layer is concentrated to recover the ketone solvent and methallyl chloride. The concentrate is washed with water to remove the unreacted catechol therefrom and then distilled in a vacuum to isolate the desired monoether.

As compared with the conventional processes, the process of this invention has the advantages that it uses solvents and catalysts which are less expensive and more readily available, achieves higher reactivity, produces a smaller amount of diether, attains a higher yield (relative to the catechol used for the reaction) and higher selectivity (i.e. yield based on the catechol converted) within a shorter period of time and further permits recovery of catechol and catalyst with greater ease.

Especially the use of ketone-water mixture as the solvent has overcome the extreme difficulties heretofore encountered in recovering the unreacted catechol and catalyst.

It is well known that catechol is inherently sensitive to heat. Although it may be possible to recover catechol by extraction, catechol will be deteriorated if the extract is heated for a long period of time for the removal of the solvent. In this respect, the present process is very advantageous because it does not require any cumbersome step of extraction or recovering the extracting solvent or heating that would lead to the deterioration of catechol.

For a better understanding of the invention examples and comparison examples are given below.

EXAMPLES 1 TO 10 AND COMPARISON EXAMPLE 1

Into a 200 ml glass reactor equipped with a thermometer, stirrer and reflux condenser were placed 10 g (91 m mole) of catechol and acetone. Then, potassium carbonate and potassium iodide were added to the mixture with stirring, and nitrogen gas was introduced into the reactor to replace the air therein. The mixture was heated to reflux temperature, and 8.24 g (91 m mole) of methallyl chloride was added dropwise over a period of 10 minutes. The mixture continuously heated under reflux.

After the reaction was completed, the reaction mixture was cooled to room temperature and filtered, and the resulting crystals were washed with a small amount of acetone. The resulting acetone solution was mixed with the filtrate. A portion of the mixed solution was diluted and analysed by high-speed liquid chromatograpy. The results are summarized in Table 1.

Another portion of the mixed solution was treated for further analysis. The acetone and methallyl chloride were removed from the solution at a reduced pressure. The concentrate was extracted with chloroform and water. The chloroform layer was dried with magnesium sulfate, concentrated and distilled at a reduced pressure to obtain monoether and diether which were identified by NMR spectrum and mass spectrum. The unreacted catechol was recovered from the water layer. These results were coincident with those obtained by the analysis with high-speed liquid chromatography. In a comparison example, acetone was used in an amount outside the range specified by the invention. The result is also given in Table 1.

The results were shown in respect of yield, selectivity and mono/di ratio (ratio of monoether to diether). These are defined as follows.

(1) Yield is the percent ratio of the number of moles of the resulting monoether to that of catechol used.
(2) Selectivity is the percent ratio of the number of moles of the resulting monoether to that of catechol consumed.
(3) Mono/di ratio is that of the resulting monoether to the resulting diether in terms of molar amount.

TABLE 1

| | Acetone (g) | $K_2CO_3$ (mM) | KI (mM) | reflux time (Hr) | Monoether yield (%) | selec. (%) | Mono/Di ratio |
|---|---|---|---|---|---|---|---|
| Com. EX. 1 | 9.4 | 91 | 91 | 30 | 45 | 49 | 2.4 |
| EX. 1 | 15.1 | 91 | 91 | 30 | 51 | 63 | 6.0 |
| 2 | 20.6 | 91 | 91 | 30 | 57 | 79 | 8.7 |
| 3 | 31.6 | 91 | 91 | 30 | 69 | 83 | 15.5 |
| 4 | 63.2 | 91 | 91 | 30 | 61 | 85 | 19.4 |
| 5 | 98.5 | 91 | 91 | 30 | 47 | 80 | 12.7 |
| 6 | 15.1 | 45 | 45 | 15 | 59 | 76 | 11.8 |
| 7 | 20.6 | 45 | 45 | 15 | 74 | 82 | 21.0 |
| 8 | 31.6 | 45 | 45 | 15 | 86 | 95 | 35.2 |
| 9 | 63.2 | 45 | 45 | 15 | 72 | 89 | 26.4 |
| 10 | 98.5 | 45 | 45 | 15 | 56 | 83 | 15.1 |

EXAMPLES 11 TO 13 AND COMPARISON EXAMPLES 2 TO 3

Into the same reactor as used in Example 1 were placed 11.0 g (100 m mole) of catechol and 34.8 g of acetone. Then, 8.2 g (49.6 m mole) of potassium iodide and potassium carbonate were added to the mixture with stirring, and the air in the reactor was replaced by nitrogen. The mixture was heated to reflux temperature, and 9.05 g (100 m mole) of methallyl chloride was added over a period of 10 minutes. The mixture was heated for 15 hours with reflux. The results are given in Table 2.

TABLE 2

| | $K_2CO_3$ (m mole) | Monoether Yield (%) | Selec. (%) | Mono/Di Ratio |
|---|---|---|---|---|
| Comp. Ex. 2 | 25 | 43 | 71 | 9.3 |
| Example 11 | 35 | 61 | 83 | 17.3 |
| 12 | 55 | 84 | 90 | 30.2 |
| 13 | 100 | 65 | 81 | 14.3 |
| Comp. Ex. 3 | 150 | 49 | 69 | 6.0 |

EXAMPLES 14 TO 17 AND COMPARISON EXAMPLE 4

Reactions were conducted in a similar manner to Examples 11 to 13 with the exception of using 6.84 g (49.6 m mole) of potassium carbonate and potassium iodide in the amounts listed in Table 3 below. The results were shown in Table 3.

TABLE 3

| | KI (m mole) | Monoether Yield (%) | Selec. (%) | Mono/Di Ratio |
|---|---|---|---|---|
| Example 14 | 1 | 65 | 82 | 11.3 |
| 15 | 25 | 75 | 82 | 15.8 |
| 16 | 55 | 84 | 89 | 31.6 |
| 17 | 100 | 72 | 80 | 14.7 |
| Comp. Ex. 4 | 150 | 57 | 75 | 9.6 |

EXAMPLES 18 TO 25

Reactions were conducted in a similar manner to Examples 1 to 10. The results were shown in Table 4.

5-nonene, 1,5-diaza-bicyclo[4,2,0]-5-octene, 1,4,-diaza-bicyclo[3,3,0]-4-octene, 3-methyl-1,4-diaza-bicyclo[3,3,0]-4-octene, etc.

Examples of amines of the above formula are ethylamine, diethylamine, triethylamine, cyclohexylamine, butylamine, hexylamine, dicyclohexylamine, methylamine, dimethylamine, piperidine, etc.

According to the invention, alkali metal carbonates or alkaline earth metal bicarbonates are used in an amount of about 0.3 to about 1 mole, preferably about 0.4 to about 0.7 mole, per mole of catechol, or alkali metal bicarbonates are used in an amount of about 0.6 to about 3 moles, preferably about 0.8 to about 1.4 moles, per mole of catechol. About 0.3 to about 3 moles of amines at least 10 pKa are used per mole of catechol.

With the present invention, at least one of iodides of alkali metals or alkaline earth metals, hydrogen iodide and methallyl iodide is usable as a catalyst. Examples of useful iodides of alkali metals and alkaline earth metals are LiI, NaI, KI, RbI, CsI, BeI$_2$, MgI$_2$, CaI$_2$, BaI$_2$, etc., among which KI and NaI are especially preferable.

In the reaction system, the catalyst reacts as represented by Equation (1) to form highly reactive methallyl iodide, which then reacts as shown by Equation (2) to form the monoether, giving the catalyst in the initial state.

Hydrogen iodide, when used, reacts first with the base in the reaction system as represented by Equation (3), giving KI, which thereafter repeatedly undergoes the reactions of Equations (1) and (2).

Methallyl iodide undergoes the reaction of Equation (2), followed by the reactions of Equations (1) and (2) repeatedly.

Usually about 0.01 to about 1 mole, preferably about 0.3 to about 0.7 mole, of the catalyst is used per mole of catechol.

The ketones useful in this invention are those represented by the formula

R$^7$COR$^8$ wherein R$^7$ is alkyl having 1 to 6 carbon atoms, R$^8$ is alkyl having 1 to 6 carbon atoms or phenyl, or R$^7$ and R$^8$ may be joined together to form alkylene having 4 to 8 carbon atoms. Examples of useful ketones are acetone, methyl ethyl ketone, diethyl ketone, methyl isobutyl ketone, dipentyl ketone, cyclohexanone, acetophenone, etc.

When such a ketone solvent is used in this invention, it is preferable to use about 1 to about 10 parts by weight of the ketone per part by weight of catechol. Alternatively when a ketone-water mixture solvent is used, it is desirable to use about 1 to about 10 parts by weight of the ketone and about 0.1 to about 10 parts by weight of water, per part by weight of catechol.

The reaction of the invention is conducted preferably at a temperature of about 50° to about 150° C. When the reaction is conducted at an increased pressure, the pressure is not particularly limited since the pressure varies greatly with the kind of the solvent and the reaction temperature.

The present invention can be practiced batchwise or continuously.

The mode of practicing the present invention will be described in greater detail.

The reaction to be carried out with use of a ketone solvent will be described first. Catechol, methallyl chloride and the desired solvent, base and catalyst are wholly mixed together in the desired order while cool, and the mixture is thereafter heated. Alternatively the mixture, other than methallyl chloride, is heated first, and methallyl chloride is thereafter admixed with the hot mixture.

After the reaction, the reaction mixture is cooled to room temperature. Crystals, if present, are filtered off and then washed with a small amount of solvent. The solvent is combined with the filtrate. The crystals comprise, for example, an alkali metal carbonate, alkali metal bicarbonate, alkali metal chloride and alkali metal iodide and are reusable as such or after treatment. The alkali metal chloride, even if contained in a large amount in the crystals, presents no particular problem to the reuse of the crystals. When desired, a small amount of water is added to the crystals, the mixture is heated to cause the salts other than the alkali metal chloride to dissolve in the water while hot utilizing the solubility difference involved, and the small amount of the aqueous solution is removed for the reuse of the crystals.

On the other hand, the solvent and methallyl chloride are removed from the filtrate in a vacuum, and the remaining catechol is extracted from the residue with water. The aqueous layer is reused after a small amount of water is removed therefrom. While the monoether only can be isolated from the oil layer by distillation, the oil layer is usable as it is for the subsequent rearrangement and cyclization reaction for preparing 2,3-dihydro-2,2-dimethyl-7-hydroxybenzofuran.

When a ketone-water mixture solvent is used, the materials may be mixed together in the same manner as when the ketone solvent is used. With the progress of the reaction, the reaction mixture separates into two layers, namely an aqueous layer and an organic layer containing the monoether. While the aqueous layer contains the unreacted base, catalyst and the chloride formed by the reaction, the layer is reused as it is or after being treated by one of the methods (a) to (c)

already described. The organic layer is concentrated to recover the ketone solvent and methallyl chloride. The concentrate is washed with water to remove the unreacted catechol therefrom and then distilled in a vacuum to isolate the desired monoether.

As compared with the conventional processes, the process of this invention has the advantages that it uses solvents and catalysts which are less expensive and more readily available, achieves higher reactivity, produces a smaller amount of diether, attains a higher yield (relative to the catechol used for the reaction) and higher selectivity (i.e. yield based on the catechol converted) within a shorter period of time and further permits recovery of catechol and catalyst with greater ease.

Especially the use of ketone-water mixture as the solvent has overcome the extreme difficulties heretofore encountered in recovering the unreacted catechol and catalyst.

It is well known that catechol is inherently sensitive to heat. Although it may be possible to recover catechol by extraction, catechol will be deteriorated if the extract is heated for a long period of time for the removal of the solvent. In this respect, the present process is very advantageous because it does not require any cumbersome step of extraction or recovering the extracting solvent or heating that would lead to the deterioration of catechol.

For a better understanding of the invention examples and comparison examples are given below.

EXAMPLES 1 TO 10 AND COMPARISON EXAMPLE 1

Into a 200 ml glass reactor equipped with a thermometer, stirrer and reflux condenser were placed 10 g (91 m mole) of catechol and acetone. Then, potassium carbonate and potassium iodide were added to the mixture with stirring, and nitrogen gas was introduced into the reactor to replace the air therein. The mixture was heated to reflux temperature, and 8.24 g (91 m mole) of methallyl chloride was added dropwise over a period of 10 minutes. The mixture continuously heated under reflux.

After the reaction was completed, the reaction mixture was cooled to room temperature and filtered, and the resulting crystals were washed with a small amount of acetone. The resulting acetone solution was mixed with the filtrate. A portion of the mixed solution was diluted and analysed by high-speed liquid chromatograpy. The results are summarized in Table 1.

Another portion of the mixed solution was treated for further analysis. The acetone and methallyl chloride were removed from the solution at a reduced pressure. The concentrate was extracted with chloroform and water. The chloroform layer was dried with magnesium sulfate, concentrated and distilled at a reduced pressure to obtain monoether and diether which were identified by NMR spectrum and mass spectrum. The unreacted catechol was recovered from the water layer. These results were coincident with those obtained by the analysis with high-speed liquid chromatography. In a comparison example, acetone was used in an amount outside the range specified by the invention. The result is also given in Table 1.

The results were shown in respect of yield, selectivity and mono/di ratio (ratio of monoether to diether). These are defined as follows.

(1) Yield is the percent ratio of the number of moles of the resulting monoether to that of catechol used.
(2) Selectivity is the percent ratio of the number of moles of the resulting monoether to that of catechol consumed.
(3) Mono/di ratio is that of the resulting monoether to the resulting diether in terms of molar amount.

TABLE 1

| | Acetone (g) | $K_2CO_3$ (mM) | KI (mM) | reflux time (Hr) | Monoether yield (%) | Monoether selec. (%) | Mono/Di ratio |
|---|---|---|---|---|---|---|---|
| Com. EX. 1 | 9.4 | 91 | 91 | 30 | 45 | 49 | 2.4 |
| EX. 1 | 15.1 | 91 | 91 | 30 | 51 | 63 | 6.0 |
| 2 | 20.6 | 91 | 91 | 30 | 57 | 79 | 8.7 |
| 3 | 31.6 | 91 | 91 | 30 | 69 | 83 | 15.5 |
| 4 | 63.2 | 91 | 91 | 30 | 61 | 85 | 19.4 |
| 5 | 98.5 | 91 | 91 | 30 | 47 | 80 | 12.7 |
| 6 | 15.1 | 45 | 45 | 15 | 59 | 76 | 11.8 |
| 7 | 20.6 | 45 | 45 | 15 | 74 | 82 | 21.0 |
| 8 | 31.6 | 45 | 45 | 15 | 86 | 95 | 35.2 |
| 9 | 63.2 | 45 | 45 | 15 | 72 | 89 | 26.4 |
| 10 | 98.5 | 45 | 45 | 15 | 56 | 83 | 15.1 |

EXAMPLES 11 TO 13 AND COMPARISON EXAMPLES 2 TO 3

Into the same reactor as used in Example 1 were placed 11.0 g (100 m mole) of catechol and 34.8 g of acetone. Then, 8.2 g (49.6 m mole) of potassium iodide and potassium carbonate were added to the mixture with stirring, and the air in the reactor was replaced by nitrogen. The mixture was heated to reflux temperature, and 9.05 g (100 m mole) of methallyl chloride was added over a period of 10 minutes. The mixture was heated for 15 hours with reflux. The results are given in Table 2.

TABLE 2

| | $K_2CO_3$ (m mole) | Monoether Yield (%) | Monoether Selec. (%) | Mono/Di Ratio |
|---|---|---|---|---|
| Comp. Ex. 2 | 25 | 43 | 71 | 9.3 |
| Example 11 | 35 | 61 | 83 | 17.3 |
| 12 | 55 | 84 | 90 | 30.2 |
| 13 | 100 | 65 | 81 | 14.3 |
| Comp. Ex. 3 | 150 | 49 | 69 | 6.0 |

EXAMPLES 14 TO 17 AND COMPARISON EXAMPLE 4

Reactions were conducted in a similar manner to Examples 11 to 13 with the exception of using 6.84 g (49.6 m mole) of potassium carbonate and potassium iodide in the amounts listed in Table 3 below. The results were shown in Table 3.

TABLE 3

| | KI (m mole) | Monoether Yield (%) | Monoether Selec. (%) | Mono/Di Ratio |
|---|---|---|---|---|
| Example 14 | 1 | 65 | 82 | 11.3 |
| 15 | 25 | 75 | 82 | 15.8 |
| 16 | 55 | 84 | 89 | 31.6 |
| 17 | 100 | 72 | 80 | 14.7 |
| Comp. Ex. 4 | 150 | 57 | 75 | 9.6 |

EXAMPLES 18 TO 25

Reactions were conducted in a similar manner to Examples 1 to 10. The results were shown in Table 4.

TABLE 4

| EX. | Catechol (mM) | Methallyl chloride (mM) | Base (mM) | | Catalyst (mM) | | Ketone (g) | | °C. × Hr | Monoether yield (%) | Monoether selec. (%) | Mono/Di ratio |
| --- | --- | --- | --- | --- | --- | --- | --- | --- | --- | --- | --- | --- |
| 18 | 91 | 91 | $K_2CO_3$ | 45 | KI | 0.9 | Acetone | 31.6 | reflux × 25 | 80 | 89 | 15.3 |
| 19 | 91 | 91 | $KHCO_3$ | 100 | KI | 45 | Acetone | 31.6 | reflux × 15 | 81 | 90 | 20.2 |
| 20 | 91 | 91 | $K_2CO_3$ | 45 | KI | 45 | Acetone | 31.6 | reflux × 20 | 89 | 94 | 31.5 |
| 21 | 91 | 91 | $Na_2CO_3$ | 45 | KI | 45 | Acetone | 31.6 | reflux × 15 | 83 | 88 | 28.7 |
| 22 | 91 | 91 | DBU | 45 | KI | 45 | Acetone | 31.6 | reflux × 20 | 82 | 91 | 26.4 |
| 23 | 91 | 91 | $(C_2H_5)_3N$ | 45 | KI | 45 | Acetone | 31.6 | reflux × 20 | 81 | 89 | 29.6 |
| 24 | 91 | 91 | $K_2CO_3$ | 45 | KI | 45 | Cyclohexanone | 31.6 | 90 × 15 | 90 | 92 | 24.9 |
| 25 | 91 | 91 | $K_2CO_3$ | 45 | KI | 45 | Methyl ethyl ketone | 31.6 | reflux × 15 | 84 | 87 | 20.4 |

EXAMPLES 26 TO 30

Into a 100-ml glass reactor equipped with a thermometer, stirrer and reflux condenser were placed 5 g (45.5 m mole) of catechol, water and ketone. Then, a base and 22.5 m mole of a catalyst were added to the mixture with stirring. The air in the reactor was replaced by nitrogen. The mixture was heated, and 4.12 g (45.5 m mole) of methallyl chloride was added dropwise over a period of 10 minutes at a prescribed temperature. The heating was continued. After completion of the reaction, the reaction mixture was cooled, and oil and water layers were analysed by high-speed liquid chromatography. The oil layer was also washed with water, dried and distilled at a reduced pressure to obtain fractions. Monoether and diether were identified by NMR spectrum and mass spectrum of fractions. The results were given in Table 5.

TABLE 5

| EX. | Solvent mixture Ketone | Solvent mixture $H_2O$-ketone (g) | Base (mM) | | Catalyst | °C. × Hr | Monoether yield (%) | Monoether selec. (%) | Mono/Di ratio |
| --- | --- | --- | --- | --- | --- | --- | --- | --- | --- |
| 26 | Acetone | 5 g–11.9 g | $KHCO_3$ | 45 | KI | reflux × 15 | 75 | 85 | 15.5 |
| 27 | Acetone | 7.5 g–9.9 g | $K_2CO_3$ | 22.5 | KI | reflux × 15 | 82 | 86 | 26.4 |
| 28 | Acetone | 10 g–7.9 g | $K_2CO_3$ | 22.5 | KI | reflux × 10 | 79 | 91 | 18.7 |
| 29 | Methyl ethyl ketone | 7.5 g–9.9 g | $K_2CO_3$ | 22.5 | KI | reflux × 10 | 78 | 88 | 20.8 |
| 30 | Diethyl ketone | 7.5 g–9.9 g | $Na_2CO_3$ | 22.5 | NaI | 80 × 15 | 75 | 87 | 19.5 |

EXAMPLE 31

Into the same reactor as used in Example 26 were placed 5 g (45.5 m mole) of catechol, a mixed solvent of water (7.5 g) and acetone (9.9 g), 6.2 g (45 m mole) of potassium carbonate and 3.74 g (22.5 m mole) of potassium iodide. The mixture was stirred, and the air in the reactor was replaced by nitrogen. The mixture was heated to reflux temperature, and 4.12 g (44.5 m mole) of methallyl chloride was added dropwise over a period of 10 minutes. The heating was continued for 15 hours under reflux.

The reaction mixture was cooled and separated into oil and water layers. The oil layer was washed with 5 g of water. The reactor was also washed with water. Both water layers were combined. The oil layer was distilled at a reduced pressure, giving acetone and 0.46 g (5.1 m mole) of methallyl chloride, which were then mixed with the water layer. The residue was found to contain 5.45 g (33.22 m mole) of monoether and 0.56 g (2.55 m mole) of diether. The water layer contained 0.55 g (5.0 m mole) of unreacted catechol remaining therein but neither of monoether and diether. Yield was 73%, selectivity 82% and mono/di ratio 12.9.

To the above water layer was added a starting material, i.e., 4.46 g (40.5 m mole) of catechol. The mixture was heated to reflux temperature, and 3.66 g (40.4 m mole) of methallyl chloride was added dropwise over a period of 10 minutes. The reaction was continued for 15 hours under reflux. Yield was 76%, selectivity 85% and mono/di ratio 18.3.

EXAMPLE 32

Reaction was carried out in the same conditions as in Example 27. The reaction mixture was cooled and separated into an oil layer and a water layer containing a precipitate. The oil layer was washed with a small amount of water, and the washings were combined with the above water layer. The combined water layer was cooled to 5° C. The crystals separating out were collected by filtration and washed with a very small amount of water. The crystals contained 1.94 g (26.1 m mole) of potassium chloride. To the reactor were returned the filtrate and the water resulted from washing the crystals, and reaction was conducted under a nitrogen atmosphere in the same manner as in Example 27 with respect to the amounts of acetone, catechol, potassium carbonate and methallyl chloride used, dropping of methallyl chloride, reaction conditions and treatment of the resulting reaction mixture except that a catalyst and water were not added. Yield was 84%, selectivity 87% and mono/di ratio 17.3.

EXAMPLE 33

Reaction was carried out under the same conditions as in Example 27. The reaction mixture was cooled to room temperature and separated into an oil layer and a water layer containing a precipitate. The oil layer was washed with a small amount of water, and the washings were combined with the above water layer. To the reactor was returned the combined water layer, and reaction was conducted under a nitrogen atmosphere in the same manner as in Example 27 with respect to the amounts of acetone, catechol, potassium carbonate and methallyl chloride used, dropping of methallyl chloride, reaction conditions and treatment of the resulting reaction mixture except that a catalyst and water were not added. Yield was 81%, selectivity 86% and mono/di ratio 19.7.

EXAMPLE 34

To the water layer obtained from the reaction in Example 33 (containing the washings used for the oil layer), was added 22.5 m mole of sodium carbonate. The mixture was heated to reflux temperature with stirring. The mixture was filtered in a hot state and the crystals were collected and washed with a small amount of hot water. The crystals were a mixture of sodium chloride and potassium chloride and contained 42.8 m mole of chlorine ions which corresponded to 95% of chlorine ions resulting from one cycle of reaction.

A large amount of precipitate separated out from a combined mixture of the filtrate and the water resulting from washing the crystals. To the reactor was returned the precipitate, and reaction was conducted under a nitrogen atmosphere in the same manner as in Example 27 with respect to the amounts of acetone, catechol and methallyl chloride used, the method of dropping of methallyl chloride, reaction conditions and treatment of the resulting reaction mixture except that potassium carbonate, catalyst and water were not added. Yield was 82%, selectively 85% and mono/di ratio 20.2.

EXAMPLES 35 TO 37

Into a 100 ml glass reactor equipped with a thermometer, stirrer and reflux condenser were placed 5 g (45.5 m mole) of catechol, water and ketone. Then, base and catalyst were added to the mixture with stirring, and the air in the reactor was replaced by nitrogen. The mixture was heated and 4.12 g (45.5 m mole) of methallyl chloride was added dropwise over a period of 30 minutes at a prescribed temperature and the heating was continued. After completion of the reaction, the reaction mixture was cooled, and oil and water layers were analysed by high-speed liquid chromatography. The results were shown in Table 6.

EXAMPLE 38

Into the same reactor as in Example 1 were placed 11.0 g (100 m mole) of catechol and 34.8 g of acetone. To the mixture were added 7.59 g (55 m mole) of potassium carbonate and 9.05 g (100 m mole) of methallyl chloride with stirring and the air in the reactor was replaced by nitrogen. To the mixture was added 1.27 g (5 m mole) of 50% hydriodic acid and the mixture was heated to reflux temperature over a period of 30 minutes, and the heating was continued for 15 hours. The results were 66% of yield, 79% selectivity and 12.7 mono/di ratio.

EXAMPLE 39

The reaction was conducted in the same manner as in Example 38 except that 0.91 g (5 m mole) of methallyl iodide was used in place of 50% hydriodic acid. Yield was 73%, selectivity 83% and mono/di ratio 11.9.

EXAMPLE 40

The reaction was carried out in the same manner as in Example 15 with the exception of using 7.34 g (25 m mole) of $CaI_2$ in place of KI. The results were 78% of yield, 88% selectivity and 19.1 mono/di ratio.

We claim:

1. A process for preparing o-methallyloxyphenol characterized in that catechol and methallyl chloride are reacted with use of:
    A. at least one base selected from among carbonates and bicarbonates of alkali metals, bicarbonates of alkaline earth metals and amines at least 10 in pKa,
    B. at least one catalyst selected from among iodides of alkali metals or alkaline earth metals, hydrogen iodide and methallyl iodide, and
    C. a ketone solvent in an amount of about 2 to about 10 parts by weight per part by weight of catechol.

2. A process as defined in claim 1 wherein the solvent is a mixture of ketone and water.

3. A process as defined in claim 1 wherein the carbonate or bicarbonate of alkali metal, or bicarbonate of alkaline earth metal is $K_2CO_3$, $Na_2CO_3$, $KHCO_3$, $NaHCO_3$ or $Ca(HCO_3)_2$.

4. A process as defined in claim 1 wherein the amines at least 10 in pKa are cyclic amidines represented by the formula wherein $R^1$ and $R^2$ are each hydrogen or alkyl having 1 to 5 carbon atoms, or are joined together to form alkyl-

TABLE 6

| | Solvent mixture | | Base | Catalyst | | | Monoether | | Mono/Di |
| --- | --- | --- | --- | --- | --- | --- | --- | --- | --- |
| EX. | Ketone | H$_2$O-ketone (g) | (mM) | | (mM) | °C. × Hr | yield (%) | selec. (%) | ratio |
| 35 | Methyl isobutyl ketone | 5 g–11.9 g | K$_2$CO$_3$ 22.5 | NaI | 22.5 | reflux × 8 | 81 | 83 | 19.5 |
| 36 | Cyclohexanone | 2.5 g–14.5 g | K$_2$CO$_3$ 22.5 | KI | 13.7 | reflux × 15 | 85 | 87 | 21.0 |
| 37 | Cyclohexanone | 2.5 g–14.5 g | K$_2$CO$_3$ 22.5 | KI | 4.5 | reflux × 15 | 80 | 88 | 20.3 | ene having 2 to 11 carbon atoms, and $R^3$ is alkylene having 2 to 6 carbon atoms, and amines represented by the formula wherein $R^4$ and $R^5$ are each hydrogen, alkyl having 1 to 8 carbon atoms or cycloalkyl having 5 to 8 carbon atoms, or are joined together to form alkylene having 5 to 8 carbon atoms, and $R^6$ is hydrogen, alkyl having 1 to 8 carbon atoms or phenyl.

5. A process as defined in claim 4 wherein the amidine is 1,8-diaza-bicyclo[5,4,0]-7-undecene, 1,6-diaza-bicyclo[4,3,0]-5-nonene, 1,5-diaza-bicyclo[4,2,0]-5-octene, 1,4-diaza-bicyclo[3,3,0]-4-octene or 3-methyl-1,4-diaza-bicyclo[3,3,0]-4-octene.

6. A process as defined in claim 4 wherein the amine is methylamine, dimethylamine, ethylamine, diethylamine, triethylamine, butylamine, hexylamine, cyclohexylamine, dicyclohexylamine or piperidine.

7. A process as defined in claim 1 wherein the iodide of alkali metal or alkaline earth metal is LiI, NaI, KI, RbI, CsI, BeI$_2$, MgI$_2$, CaI$_2$, SrI$_2$ or BaI$_2$.

8. A process as defined in claim 1 wherein the catalyst is KI or NaI.

9. A process as defined in claim 1 wherein the ketones are those represented by the formula wherein $R^7$ is alkyl having 1 to 6 carbon atoms, $R^8$ is alkyl having 1 to 6 carbon atoms or phenyl, or $R^7$ and $R^8$ may be joined together to form alkylene having 4 to 8 carbon atoms.

10. A process as defined in claim 2 wherein the reaction mixture is separated into an aqueous layer and an organic layer, and the aqueous layer is used again for the reaction as it is or after treating the layer.

11. A process as defined in claim 1 wherein methallyl chloride is used in an amount of about 0.6 to about 1.4 moles per mole of catechol.

12. A process as defined in claim 1 wherein the alkali metal carbonate or alkaline earth metal bicarbonate is used in an amount of about 0.3 to about 1 mole per mole of catechol.

13. A process as defined in claim 1 wherein the alkali metal bicarbonate is used in an amount of about 0.6 to about 3 moles per mole of catechol.

14. A process as defined in claim 1 wherein the amine at least 10 in pKa is used in an amount of about 0.3 to about 3 moles per mole of catechol.

15. A process as defined in claim 1 wherein the catalyst is used in an amount of about 0.01 to 1 mole per mole of catechol.

16. A process as defined in claim 2 wherein about 1 to about 10 parts by weight of the ketone and about 0.1 to about 10 parts by weight of water are used per part by weight of catechol.

17. A process as defined in claim 1 wherein the reaction is conducted at about 50° to 150° C.

* * * * *